United States Patent [19]

Kantrowitz et al.

[11] Patent Number: 4,913,700
[45] Date of Patent: Apr. 3, 1990

[54] CULTURE AND TRANSPORT ASSEMBLY FOR PERCUTANEOUS ACCESS DEVICE

[75] Inventors: Adrian Kantrowitz, Pontiac; Paul S. Freed, Bloomfield Hills, both of Mich.

[73] Assignee: L. Vad Technology, Inc., Pontiac, Mich.

[21] Appl. No.: 259,991

[22] Filed: Oct. 21, 1988

Related U.S. Application Data

[63] Continuation-in-part of Ser. No. 116,311, Apr. 11, 1987, Pat. No. 4,810,246.

[51] Int. Cl.$^4$ ............................................. A61M 5/00
[52] U.S. Cl. ...................................... 604/93; 206/438; 435/287
[58] Field of Search ............... 604/93, 175, 174, 891.1; 206/363, 438; 435/809, 810, 287

[56] References Cited

U.S. PATENT DOCUMENTS 4,092,983 6/1978 Slivenko .
4,164,221 8/1979 Bentley et al. .
4,605,007 8/1986 Heraly ........................... 128/419 PT
4,634,422 1/1987 Kantrowitz et al. ................ 604/49
4,668,222 5/1987 Poirier ................................. 604/175

Primary Examiner—Stephen C. Pellegrino
Attorney, Agent, or Firm—Basile and Hanlon

[57] ABSTRACT

A culture and transport assembly for enclosing a percutaneous access device within a sealed outer container to maintain the device under sterile conditions during transport while accommodating culturing of a coating of dermal cells on a portion of the device while the device is retained within the container. The container has a removable cap to which a culture well body is attached. The percutaneous access device is releasably clamped between the bottom of the body and an underlying platform with a portion of the device projecting into a bore in the body. When the device is so clamped, the bore constituted a sealed culture chamber in which the dermal cell culturing procedure may be performed by introducing cells and culturing solutions into the chamber via fluid passages extending from the chamber to connectors accessible at the exterior of the cap.

6 Claims, 1 Drawing Sheet

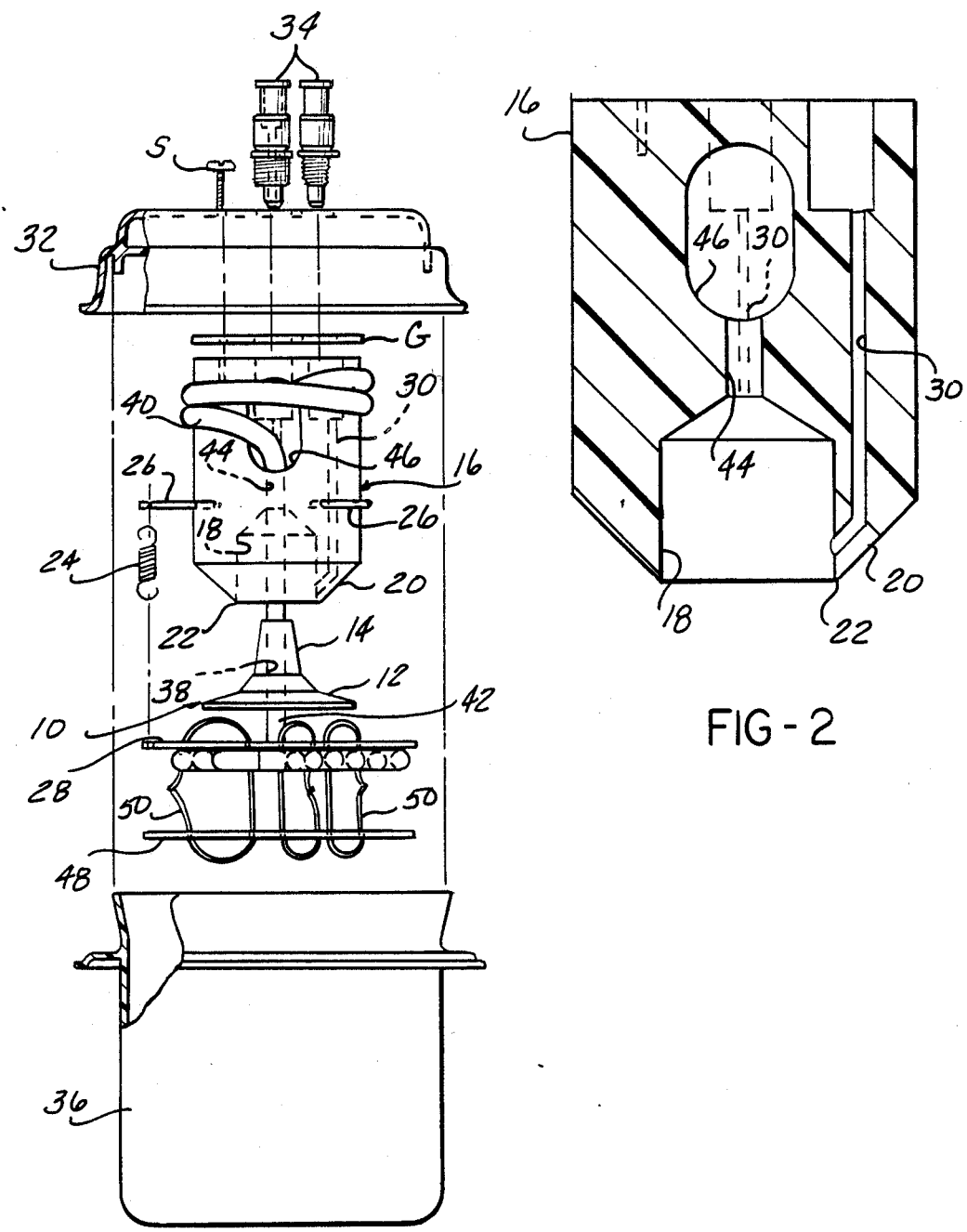

CULTURE AND TRANSPORT ASSEMBLY FOR PERCUTANEOUS ACCESS DEVICE

BACKGROUND OF THE INVENTION

1. Field of the Invention

The present invention is directed to a culture and transport assembly for a percutaneous access device which will enable the culturing of a fibroblast layer upon a selected portion of the access device and the shipping or transport of the access device without removal of the access device from the container in which it is sealed when manufactured.

2. Description of the Related Art

In U.S. Pat. No. 4,634,422 there is disclosed a percutaneous access device, a method for culturing a fibroblast layer upon a selected portion of that device, and a method for implanting the device in a human body. As described in that patent, a percutaneous access device is employed to establish a fluid or electrical connection through the skin of a patient from an external device to an organ or device implanted within the patient's body. The percutaneous access device must project through the patient's skin and the epidermis will attempt to close the opening through which the access device projects. This natural action of the epidermis can eventually marsupialize and tend to extrude the entire access device or, more typically, create sinus tracks which provide ideal conditions for the development of infection.

The foregoing problem was addressed by the subject matter of Patent 4,634,422 by utilizing apparatus and methods which enable a firm bond to be formed between the dermal layer of the patient's skin and the implanted access device which blocks downward growth of the epidermal layer along the sides of the device. As disclosed in that patent, the access device was constructed with a detectable sleeve which, when assembled on the device, formed that portion of the device which projected through the dermal layer when the device was implanted. In preparation for implantation, the sleeve was removed from the access device and a multi-layer coating of dermal cells was cultured on the external surface of the sleeve under laboratory conditions, by a procedure described in Patent 4,634,422. The sleeve, with the cultured dermal cell coating, was reassembled onto the access device immediately prior to implantation.

The technique described above presented the advantage of establishing a relatively small surface area onto which the cell layer was cultured by the employment of the removable sleeve. It also enabled the cell coating to be bonded to the sleeve under controlled, sterile laboratory conditions which enabled the coating to be firmly bonded to the sleeve prior to implantation. Attempting to bond the dermal cells directly to the sleeve while implanted in the patient was not feasible because of the unavoidable movement or stretching of the patient's skin made the formation of the bond difficult. Bonding of the dermal layer cultured on the sleeve to the dermis upon implantation required but a few days, while the bonding of the dermal layer to the sleeve would normally require two or more weeks under laboratory conditions.

While the foregoing technique represented a substantial improvement over the prior art, it also presented new problems. Culturing the dermal layer upon the sleeve was performed in a laboratory which was frequently remote from the medical facility in which the implantation was performed. This required not only transport of the sleeve with its cultured layer from the laboratory to the medical facility, but also required extremely careful handling in the assembly of the sleeve upon the device just prior to implantation. At this stage, the dermal layer cultured on the exterior of the sleeve was quite thin and fragile.

The present invention is directed to a solution of these last problems.

SUMMARY OF THE INVENTION

In accordance with the present invention, the percutaneous access device of the present invention with a relatively flat base flange and an integral or fixedly attached central projection which projects upwardly from the center of the base flange and constitutes that portion of the device which will protrude through the patient's skin. The surface of the projecting portion of the access device is formed, as was the sleeve of the device of Patent 4,634,422, with a nanoporous external surface adapted, as described in greater detail in Patent 4,634,422, to facilitate the bonding of a coating of dermal cells to the nanoporous surface.

The culture and transport device of the present invention includes a disk-like platform for supporting the base flange of the access device. A polycarbonate body is formed with a relatively large diameter bore extending upwardly from the bottom of the body to define an open-bottomed culture well of a diameter such that when the body is lowered into sealed relationship with the upper surface of the base flange of the access device, and sealed around the opening of the bore to the base flange, the projecting portion of the device with its nanoporous surface is located within a sealed culture chamber defined by the well. Passages through the polycarbonate body from its upper end open into the culture well so that a fibroblast or dermal cell culture and culturing medium may be introduced into the well. Typically, these passages will include a vent passage and a fluid inlet passage. The base flange of the access device is resiliently clamped between the polycarbonate body and the platform as by tension springs stretched between the platform and pins projecting from the polycarbonate body.

At the upper end of the body, a cap or container top is fixedly secured to the body to cooperate with a cup or container bottom to define a closed container within which the polycarbonate body, access device and platform are releasably sealed. Luer-type connectors may be mounted in the cap to communicate with the passages leading to the culture well within the body so that cultures and culturing medium may be introduced into the culture well from the exterior of the sealed container.

Some types of access devices include a catheter or flexible tube which is passed through the access device to project downwardly from the base flange and upwardly from the top of the projecting portion of the access device. The platform is provided, in this case, with a central hole through which the downwardly projecting portion of the catheter can pass to be coiled flat against the underside of the platform and held in position by an underlying disk detachably connected to the platform. The polycarbonate body is provided with an opening extending from the top of the culture well to open at the side of the body so that the portion of the catheter projecting upwardly from the access device can be led to the exterior of the body and coiled around the exterior of the body beneath the container cap.

Other objects and features of the invention will become apparent by reference to the following specification and to the drawings.

BRIEF DESCRIPTION OF THE DRAWINGS

FIG. 1 is an exploded side elevational view, with certain parts broken away, of an assembly embodying the present invention; and FIG. 2 is a cross-sectional view, taken on a vertical plane of the culture well body of the assembly of FIG. 1.

DESCRIPTION OF THE PREFERRED EMBODIMENT

In the drawings, a percutaneous access device, hereinafter referred to as a "PAD, is designated generally 10 and includes a base flange 12 and a centrally located projection 14 which projects upwardly from base flange 12. The flange 12 and projection 14 are normally integrally formed with each other from a relatively soft, semi-rigid, silicone-type material. The outer surface of the projection 14 will be formed with a multiplicity of microscopic pores or recesses as by a nuclear bombardment and etching procedure as described in Patent 4,634,422.

This type of surface will be referred to as a nanoporous surface. The pores or cavities of the nanoporous surface enable ingrowth of portions of dermal cells cultured on the nanoporous surface to establish a mechanical bond between the dermal cells and projection 14. As explained in greater detail in Patent 4,634,422, the culturing and bonding of a multilayer coating of dermal cells upon projection 14 prior to the implantation of the PAD in the patient enables the formation, within a few days after implantation, of a barrier layer of dermis bonded to the dermal cells cultured on projection 14 which will prevent down growth of the overlying epidermal layer after implantation.

Formation of the desired coating of dermal cells upon the exterior surface of projection 14, by procedures described in detail in Patent 4,634,422, is a process which takes about two weeks under laboratory conditions.

In accordance with the present invention, during this culturing operation the PAD is located within a sealed container which may also be used to transport the PAD from its place of manufacture to the culturing laboratory and thence to the operating room in a sterile and protected environment.

The culture and transport device includes a polycarbonate body designated generally 16 formed with a bore 18 projecting upwardly into the body from its lower end to define an open-bottomed chamber or culture well. The diameter and depth of bore 18 are such as to enclose, with a substantial clearance, projection 14 of the PAD when body 16 is pressed downwardly onto the base flange 12 of the PAD. The lower end of body 16 is formed with an inwardly tapered frustoconical section 20 terminating at the periphery of bore 18 to define an annular peripheral sealing edge extending around the opening of bore 18 which will engage the upper surface of base flange 12 of the PAD to seal body 16 to base flange 12. Base flange 12 and projection 14 are formed of a relatively soft, resilient, silicone material which enables a fluid-tight seal between base flange 12 and body 16 to be easily effected. Tension springs 24 connected between pins 26 fixed to body 16 and openings in a base flange supporting platform 28 are employed to detachably clamp the base flange 12 of the PAD between sealing surface 22 on body 16 and the upper surface of platform 28.

Two or more passages, such as 30, are formed through body 16 to extend from bore 18 to the top of body 16. A container cap 32 is fixedly and sealingly mounted on the top of body 16, and male Luers 34 pass through the cap and are threaded into the top of body 16 to establish an externally accessible fluid communication with passages 30 in body 16. Container cap 32 is adapted to be sealingly received upon the upper end of a cup-shaped container bottom 36 to provide a sealed container enclosing the assembled body 16, PAD 10 and platform.

In the particular form of PAD 10 shown in the drawings, the PAD is formed with a central passage 38 extending vertically through both base flange 12 and projection 14. A catheter in the form of a flexible tube is received in passage 38 and has an outer portion 40 projecting upwardly from projection 14 and a lower portion 42 which projects downwardly from base flange 12. When the PAD is implanted in the patient, flange 12 is disposed beneath the patient's skin and the lower portion of the catheter 42 is led from the flange to follow the muscle layer below the hypodermis to a desired location. Projection 14 projects upwardly through the skin and the projecting portion 40 of the catheter provides flexibility in the connection between the PAD and any container or device to which the external end of the catheter may be connected. This minimizes stresses tending to shift the PAD relative to the patient upon connecting or disconnecting the end of the catheter to an external container or the like. The catheter may be employed to introduce or withdraw fluids to or from a particular body cavity during a continued course of treatment.

As indicated in the drawings, the end portion 40 of the catheter prior to implantation of the PAD is led from projection 14 through an extension 44 of bore 18 which opens into an opening 46 through the side wall of body 16. The catheter portion 40 is received in a fluid-tight sealed relation in bore 44. That portion of catheter 40 which protrudes from opening 46 may be coiled around the exterior of body 16 as illustrated beneath cap 42.

That portion 42 of the catheter which projects from the lower side of base flange 12 of the PAD is passed through a central opening in platform 28 and formed into a flat coil lying against the underside of the platform. The coiled portion of the catheter may be held in this last position by a disk 48 held in position by sutures or ties 50 which pass through openings near the outer periphery of platform 28 and disk 48 and are tied tightly to hold the coiled catheter clamped between disk 48 and platform 28.

Although the parts are shown separated in the exploded view of FIG. 1, it is believed apparent that, when assembled, cap 32 is fixedly secured to the top of body 16 as by a screw S and the threaded engagement of the connectors 34 in the enlarged upper ends of passages 30. Gaskets G are provided at appropriate locations. As stated in the foregoing description, the PAD 10 is inserted into bore 18 until the sealing lip 22 at the lower end of body 16 is engaged with the upper surface of base flange 12 of the PAD. The base flange is firmly clamped upwardly against the seal 22 by the tensile force applied by tension springs 24 which are hooked between the pins 26 and platform 28 so that base flange 12 is resiliently clamped between the seal edge 22 and the platform. As previously stated, disk 48 is tightly tied to clamp the coil of catheter 42 firmly against the bottom of platform 28. Thus, all of the elements shown in the drawing, with the exception of the cup-shaped container bottom 36, are secured to each other when the device is assembled. The various parts secured beneath the cap form an assembly which can be inserted downwardly into the container bottom 36 until cap 32 sealingly engages and is seated upon the upper end of container bottom 36.

The assembly described above is performed under sterile conditions and, for purposes of shipment, the device may be enclosed in a sealed bag to maintain sterility during shipment to the culturing laboratory.

Within the laboratory, the seal between the container cap and container bottom is adequate to maintain sterility within the container.

At the culturing laboratory, a coating of dermal cells is cultured upon projection 14, according to the procedure described in Patent 4,634,422. Normally, dermal cells and growth stimulating solutions will be introduced into the culture well defined by bore 18 via one of the connectors 34 and its associated passage 30, while another passage 30 and its associated connector 34 will function as a vent to permit the introduction of fluids into the culture well or to withdraw fluids from the well. Throughout this procedure, cap 32 remains sealed onto container bottom 36.

After the desired coating has been applied to projection 14, a process which may consume two weeks or more, the container, still in its closed condition, may again be sealed within a shipping envelope to maintain sterility and transported to the operating room in which the PAD is to be implanted. Access to the PAD is had by removing cap 32 and the attached elements from container bottom 36, cutting ties 50 to release disk 48 and the coiled portion of catheter portion 42 from platform 28, uncoiling the upper portion 40 from body 16 and finally disconnecting springs 24 to permit platform 28 to be separated and to release the PAD from body 16 by withdrawing the now uncoiled portion 40 of the catheter outwardly through bore extension 44 and bore 18.

While one embodiment of the invention has been described in detail, it will be apparent to those skilled in the art the disclosed embodiment may be modified. Therefore, the foregoing description is to be considered exemplary, rather than limiting, and the true scope of the invention is that defined in the following claims.

What is claimed is:

1. A culture and transport assembly for a PAD having a disk-like, horizontal base flange and a projection projecting vertically upwardly from the central portion of said base flange, said projection having an exterior surface adapted to have a coating of dermal cells cultured thereon and bonded to said surface,
    said culture and transport assembly comprising a horizontal platform adapted to support said base flange of said PAD thereon, a culture well body having a bore extending upwardly into said body from the lower end of said body, said bore having a depth and diameter respectively greater than the height of said projection above said base flange and the maximum horizontal dimension of said projection, sealing means on the lower end of said body sealingly engageable with said base flange to seal the lower end of said bore to the upper surface of said base flange in peripherally spaced relationship to said projection to constitute said bore as a culture well enclosing said projection, retention means for detachably clamping said base flange between said sealing means and said platform, and passage means in said body for conducting fluid between said well and the exterior of said body while said sealing means is sealingly engaged with said base flange.

2. The invention defined in claim 1 further comprising a transport container including a cap fixedly secured to and projecting outwardly from the upper end of said body, and a cap-shaped member having an open upper end adapted to be sealingly closed by said cap, said cap when sealed to said container being operable to support said body, PAD and base within said container.

3. The invention defined in claim 2 wherein said PAD further comprises an elongate flexible catheter mounted within and extending through said PAD and having a first elongate portion projecting downwardly from said base flange and a second elongate portion projecting upwardly from said projection of said PAD, said platform having a central opening therethrough through which said first portion of said catheter projects and means for releasably retaining said first portion of said catheter in a flat coiled storage position beneath said platform, said body having a catheter receiving passage extending upwardly from said well and opening through one side of said body adapted to enable said second portion to extend from said projection through said well and said body to the exterior of said body, and means for releasably retaining that part of said second portion at the exterior of said body coiled about said body beneath said cap.

4. The invention defined in claim 2 further comprising sealable connecting means mounted upon and accessible from the exterior of said cap is fluid communication with said first passage means for placing said well in fluid communication with the exterior of said container.

5. A culture and transport assembly for a PAD having a disk-like horizontal base flange and a projection projecting vertically upwardly from the central portion of said base flange, said projection having an exterior surface adapted to have a coating of dermal cells cultured thereon and bonded to said surface;
    said culture and transport assembly comprising a culture well body having a chamber therein adapted, when said body is sealed at its lower end, to said base flange to define a fluid-tight culture well enclosing said projection in spaced relation to said exterior surface, said body having an upper surface, a cap mounted on said upper surface, and means accessible from the exterior of said cap for conducting fluid through said cap and into said chamber.

6. The invention defined in claim 5 further comprising a cup-shaped container having an open upper end adapted to sealingly receive said cap to enclose said body and said PAD.

* * * * *